US00PP11408P

United States Patent [19]

Verwer

[11] Patent Number: Plant 11,408

[45] Date of Patent: Jun. 6, 2000

[54] DAHLIA PLANT NAMED 'KARMA SANGRIA'

[75] Inventor: Aad Verwer, Lisse, Netherlands

[73] Assignee: Fa. Gebr. Verwer, Lisse, Netherlands

[21] Appl. No.: 09/026,006

[22] Filed: Feb. 19, 1998

[30] Foreign Application Priority Data

Apr. 7, 1997 [NL] Netherlands ..... DHL77

[51] Int. Cl.[7] ..... A01H 5/00

[52] U.S. Cl. ..... Plt./321

[58] Field of Search ..... Plt./321

[56] References Cited

U.S. PATENT DOCUMENTS

P.P. 899 11/1949 Gilmore ..... Plt./321

OTHER PUBLICATIONS

GTITM UPOVROM Citation for 'Karma Sangria' as per NL PBR DHL0077, Apr. 7, 1997.

*Primary Examiner*—Howard J. Locker
*Assistant Examiner*—Kent L. Bell
*Attorney, Agent, or Firm*—Christie, Parker & Hale, LLP

[57] ABSTRACT

A dahlia plant producing red/purple and yellow bicolor flowers.

1 Drawing Sheet

BACKGROUND OF THE INVENTION

The present invention relates to a new and distinct variety of *Dahlia hybrida* known by the varietal denomination 'Karma Sangria'. The female parent of 'Karma Sangria' is an unpatented, undistributed seedling identified as 'VDW 57' and the male parent is the variety known as 'Alfred Grille', not known to be patented.

SUMMARY OF THE INVENTION

The new variety is a dahlia plant useful for growing outdoors and under glass which produces attractive red/purple and yellow bicolor flowers on long stems. Among the traits possessed by the new variety which in combination distinguish it from other varieties known to the inventor are its attractive flowers borne on long stems.

Asexual reproduction by cuttings of the new variety in The Netherlands has demonstrated that the combination of characteristics as described herein for 'Karma Sangria' are firmly fixed and are retained through successive generations of asexual reproduction.

COMPARISON WITH PARENT

The new variety differs from its parent 'Alfred Grille' in flower color.

BRIEF DESCRIPTION OF ILLUSTRATION

The accompanying color photographic illustration shows a typical bloom and leaves of the new variety in colors as nearly true as possible with an illustration of this type.

DESCRIPTION OF THE NEW VARIETY

In the following description, color references are to The Royal Horticultural Society Colour Chart, where color values refer to color plate numbers in this chart.

The following observations are of plants described and grown in The Netherlands under outdoor conditions which approximate those generally used in commercial practice.

'Karma Sangria' has not been observed under all possible environmental conditions. The phenotype may vary with variations in environment such as temperature, light intensity, day length and cultural conditions.

Plant:

*Form.*—Upright, spreading.

*Height.*—About 110 cm.

*Branching characteristics.*—Moderate.

*Flower stem.*—Length: About 80 to 90 cm. Color: Near 146C with anthocyanin.

*Natural flowering season.*—July to November in The Netherlands under glass.

*Disease resistance.*—Similar to the species.

*Hardiness.*—Plants are winter hardy to 0° C.

*Flowering time.*—Time to flowering from rooted cutting is about 45 to 55 days, plants are typically pinched 1 to 2 weeks after planting with the first blooms produced about 35 to 40 days later.

*Foliage.*—Quantity: Many. Size of leaf: Length: About 20 cm. Width: About 4 to 10 cm. Shape of leaf: Ovate. Leaf edge: Dentate. Leaf apex: Acute. Texture: Leaf upperside: Leathery. Leaf under side: Smooth. Color: Leaf upperside: Near 138B. Leaf under side: Near 146C. Venation: Pinnate. Petiole length: Varies; some leaves have petioles that are 5–10 cm and some leaves are sessile. Stipules: None. Petiole color: Near 79C.

Bud:

*Form.* —Globular.

*Size.*—About 1 cm.

*Opening rate.*—About 14 to 20 days.

*Color of ray florets.*—When sepals first divide near 64A; when ray florets begin to unfurl near 73A.

Flower:

*Inflorescence form.*—Blooms borne singly.

*Bloom type.*—Cactus.

*Bloom diameter.*—About 14 cm.

*Response.*—About 2 to 3 main branches are produced, with flowering occurring about 35 to 40 days later from pinch.

*Typical number of flowers harvested per plant per season.* —About 30 to 40.

*Color tonality from a distance.*—Apricot with red-purple tonality.

*Lasting quality.*—About 20 to 25 days on plant; about 10 to 12 days after cutting.

*Ray florets.*—Length: About 6.1 cm. Width: About 1.4 cm. Shape: Oblong. Apex: About 3 to 6 irregular acute lobes. Base: Rounded.

*Color.*—Bicolor; yellow at the base, red-purple at the top. Inner ray florets (upper surface and undersurface): Near 64A. Outer ray florets (upper surface and undersurface): Near 64A. Point of ray floret attachment: Near 2A extending toward the middle of each floret. As bloom ages: Colors fade to near 2C and to near 73A and 73B. Fragrance: None.

*Disc florets*.—Number: About 30. Length: About 1.3 cm. Color: Near 7A. Shape: Cylindric.

*Sepals*.—Number: About 25. Length: About 1.8 cm. Width: About 1.3 cm. Color: Near 137A. Apex: Broadly acute. Base: Rounded.

Reproductive organs:

*Stamens*.—Tubular, near 15A.

*Anthers*.—Near 15A.

*Pollen*.—Near 16A.

*Pistils*.—Styles length about 2 mm, color near 1C; stigmas divided, near 6A.

*Character of ovaries*.—1 per pistil.

I claim:

1. A new and distinct dahlia plant of the variety substantially as shown and described.

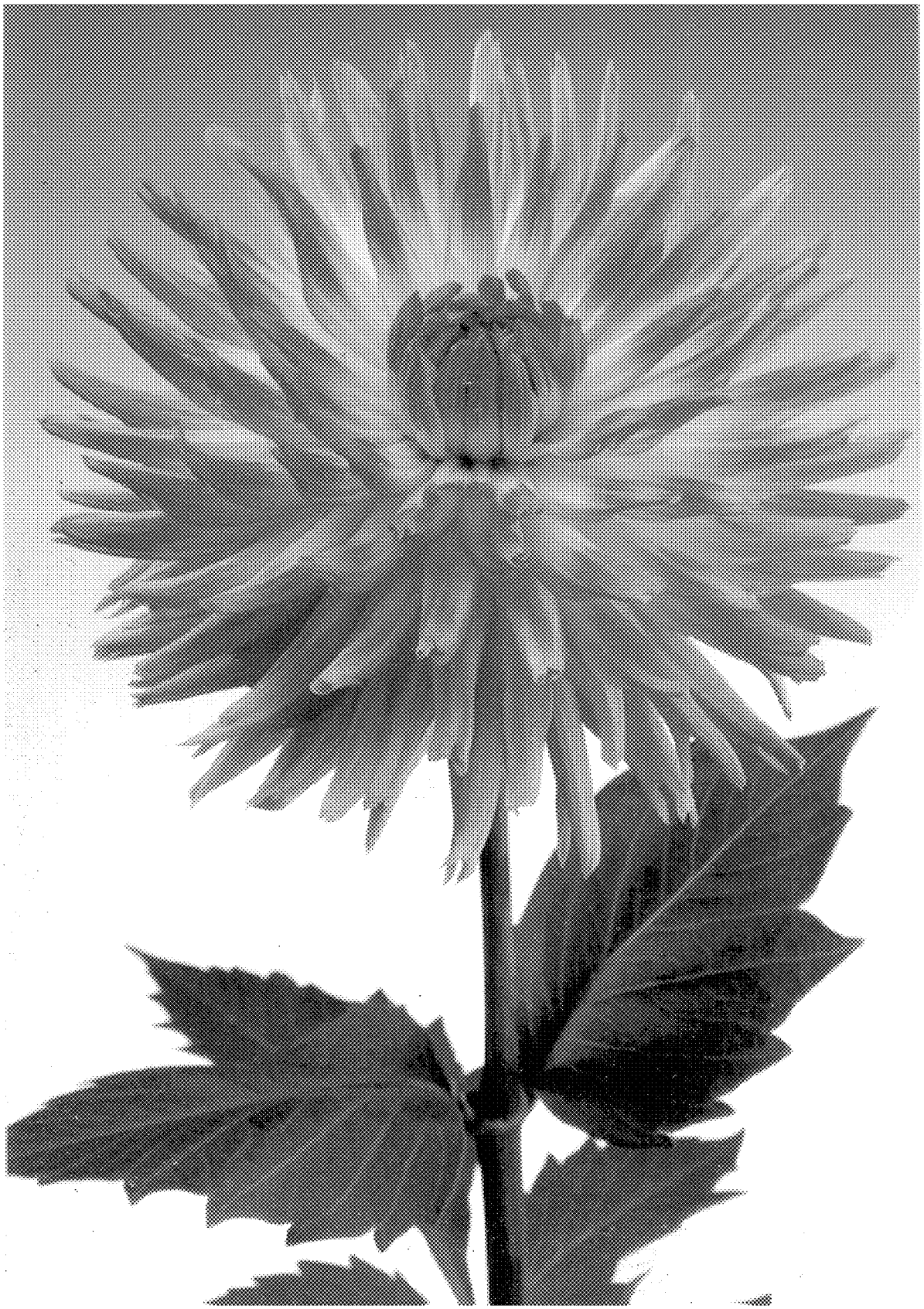

* * * * *